United States Patent
Plumptre

(10) Patent No.: US 9,440,029 B2
(45) Date of Patent: Sep. 13, 2016

(54) DRIVE MECHANISM FOR A DRUG DELIVERY DEVICE AND DRUG DELIVERY DEVICE

(75) Inventor: David Aubrey Plumptre, Droitwich Spa (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 56 days.

(21) Appl. No.: 13/825,812

(22) PCT Filed: Oct. 5, 2011

(86) PCT No.: PCT/EP2011/067416
§ 371 (c)(1),
(2), (4) Date: Aug. 8, 2013

(87) PCT Pub. No.: WO2012/045792
PCT Pub. Date: Apr. 12, 2012

(65) Prior Publication Data
US 2013/0310761 A1    Nov. 21, 2013

(30) Foreign Application Priority Data
Oct. 6, 2010   (EP) ..................................... 10186732

(51) Int. Cl.
*A61M 5/315*      (2006.01)
*A61M 5/24*       (2006.01)

(52) U.S. Cl.
CPC .......... *A61M 5/3155* (2013.01); *A61M 5/3156* (2013.01); *A61M 5/31555* (2013.01); *A61M 5/31585* (2013.01); *A61M 5/31593* (2013.01); *A61M 5/31515* (2013.01); *A61M 2005/2407* (2013.01)

(58) Field of Classification Search
CPC ........... A61M 5/31511; A61M 5/315; A61M 5/31515; A61M 5/347; A61M 2005/31508; A61M 5/3156; A61M 5/31593; A61M 5/31555; A61M 5/31585
USPC ........ 604/154, 155, 180–211, 218, 220, 224, 604/228
See application file for complete search history.

(56) References Cited

U.S. PATENT DOCUMENTS

| | | | |
|---|---|---|---|
| 2004/0267207 A1* | 12/2004 | Veasey et al. | 604/208 |
| 2008/0071227 A1 | 3/2008 | Moser et al. | |
| 2009/0043264 A1* | 2/2009 | Glejbol et al. | 604/211 |
| 2009/0240195 A1 | 9/2009 | Schrul et al. | |
| 2009/0275916 A1* | 11/2009 | Harms et al. | 604/506 |

FOREIGN PATENT DOCUMENTS

| | | |
|---|---|---|
| DE | 10237258 A1 | 3/2004 |
| EP | 1923084 A1 | 5/2008 |
| EP | 1923085 A1 | 5/2008 |
| WO | 2008058665 A1 | 5/2008 |
| WO | WO 2008058665 A1 * | 5/2008 |

\* cited by examiner

*Primary Examiner* — Kami A Bosworth
*Assistant Examiner* — Hamza Darb
(74) *Attorney, Agent, or Firm* — McDonnell Boehnen Hulbert & Berghoff LLP

(57) ABSTRACT

The drive mechanism comprises a lead screw (5) and a lead screw nut, which are aligned with an axis (4). The lead screw has screw threads (6, 16) having the same pitch and being intertwined.

9 Claims, 1 Drawing Sheet

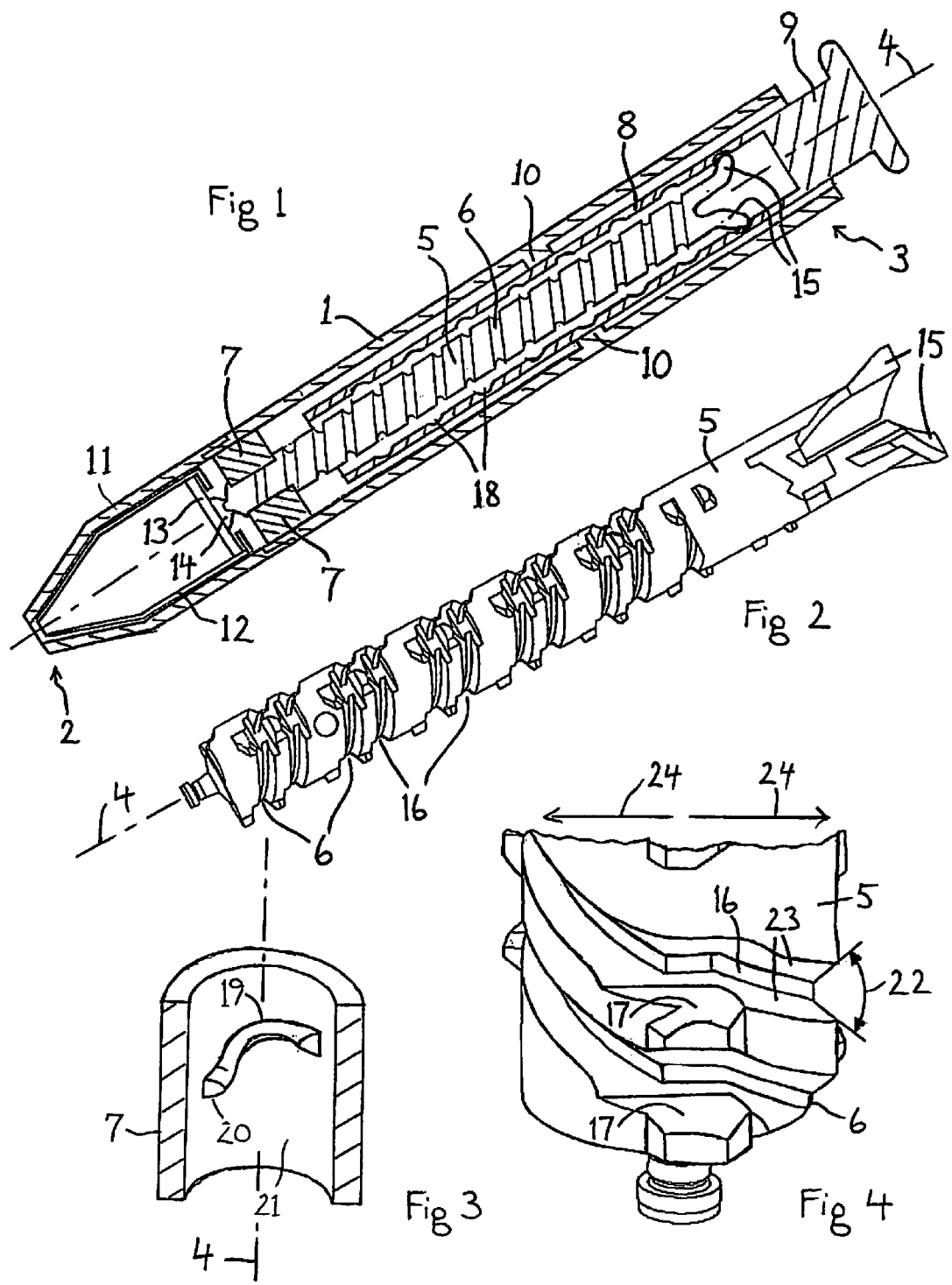

DRIVE MECHANISM FOR A DRUG DELIVERY DEVICE AND DRUG DELIVERY DEVICE

CROSS REFERENCE TO RELATED APPLICATIONS

The present application is a U.S. National Phase application pursuant to 35 U.S.C. §371 of International Application No. PCT/EP2011/067416 filed Oct. 5, 2011, which claims priority to European Patent Application No. 10186732.3 filed Oct. 6, 2010. The entire disclosure contents of these applications are herewith incorporated by reference into the present application.

FIELD OF INVENTION

The present invention relates to a drive mechanism for a drug delivery device, especially for a device that is designed for the delivery of fixed doses.

BACKGROUND

Portable drug delivery devices are used for the administration of a drug that is suitable for self-administration by a patient. A drug delivery device is especially useful in the shape of a pen, which can be handled easily and kept everywhere available. A drug is delivered by means of a drive mechanism, which may also serve to set the dose that is to be delivered. A type of drug delivery device is constructed to be refillable and thus reusable many times.

DE 102 37 258 B4 describes a drug delivery device in the shape of an injection pen, which has a drive mechanism with elements that are rotated with respect to one another around a common axis.

It is an object of the present invention to disclose a new drive mechanism for a drug delivery device and a drug delivery device comprising a new drive mechanism.

This object is achieved by a drive mechanism according to claim 1 and a drug delivery device according to claim 9, respectively. Further objects are achieved by embodiments according to the dependent claims.

SUMMARY

The drive mechanism for a drug delivery device comprises a lead screw and a lead screw nut, which are aligned with an axis defining an axial direction and an opposite axial direction. The lead screw has a screw thread and at least one further screw thread, the screw thread and the further screw thread having the same pitch and being intertwined. Thus the lead screw may have intertwined co-axial helical thread features with separate entries. A drive feature of the lead screw nut engages the screw thread and the further screw thread and allows a helical movement of the lead screw with respect to the lead screw nut at least in the axial direction.

The drive mechanism and the drug delivery device provided with the drive mechanism comprise a lead screw with a screw thread, which is preferably formed to facilitate the operation of the mechanism. One feature of the screw thread, which is a helix surrounding a central axis, may be a non-zero opening angle in the radial directions with respect to the central axis. Thereby a buttressed thread form is achieved, which facilitates a centring of the lead screw with respect to further components of the mechanism.

In an embodiment of the drive mechanism the drive feature of the lead screw nut engages the screw threads of the lead screw between surfaces of the screw threads. The surfaces of the screw threads form a non-zero angle in the radial directions diverging from the axis.

A further embodiment of the drive mechanism may further comprise a drive member, which is rotationally locked with the lead screw nut. The lead screw is coupled with the drive member, so that the coupling generates a helical movement of the lead screw with respect to the drive member when the drive member is moved in the axial direction with respect to the lead screw. The coupling is overridden to prevent a helical movement of the lead screw with respect to the drive member when the drive member is moved in the opposite axial direction with respect to the lead screw.

A further embodiment of the drive mechanism may further comprise a flexible guide feature of the lead screw and a screw thread of the drive member. The flexible guide feature of the lead screw and the screw thread of the drive member provide the coupling of the lead screw with the drive member.

In a further embodiment of the drive mechanism the screw thread of the drive member has two separate co-axial helical features.

A further embodiment of the drive mechanism comprises stop features of the lead screw. The stop features are provided to inhibit the helical movement of the lead screw when the drive member is moved in the opposite axial direction with respect to the lead screw.

In a further embodiment of the drive mechanism the drive feature of the lead screw nut comprises at least two separate parts protruding from an inner sidewall of the lead screw nut.

In a further embodiment of the drive mechanism the drive feature of the lead screw nut is tapered towards the screw thread of the lead screw.

In another aspect of the invention, a drug delivery device is provided with the drive mechanism. The drug delivery device comprises a body, which has a distal end and a proximal end, which are spaced apart in the direction of the axis of the drive mechanism.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen.

The term "distal end" refers to a part of the body or housing which is intended to be arranged at a portion of the drug delivery device from which a drug is dispensed. The term "proximal end" refers to a part of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

The term "lead screw" encompasses any element, whether unitary or of multipart construction, that is provided to transfer a movement to a piston, thus working as a piston rod, especially for the purpose of dispensing a drug. The lead screw may be flexible or not.

The drive mechanism can be used to expel a drug from a receptacle or cartridge inserted in the body of a drug delivery device. The drug delivery device can be a disposable or re-usable device designed to dispense a dose of a drug, especially a liquid, which may be insulin, a growth hormone, a heparin, or an analogue and/or a derivative thereof, for example. The drug may be administered by a needle, or the device may be needle-free. The device may be further designed to monitor physiological properties like blood glucose levels, for example. Each time the lead screw is shifted in the distal direction with respect to the body, a certain amount of the drug is expelled from the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38[Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, -continued Asp28] Exendin-4(1-39)-NH2, des Pro36, Pro37, Pro38 [Trp(O2)25, Asp28]
Exendin-4(1-39)-(Lys)6-NH2, H-(Lys)6-des Pro36, Pro37, Pro38 [Trp(O2)25
,Asp28] Exendin-4(1-39)-(Lys)6-NH2, H-Asn-(Glu)5-des Pro36, Pro37, Pro38 [Trp(O2)25,
Asp28] Exendin-4(1-39)-(Lys)6-NH2, H-(Lys)6-des Pro36 [Met(O)14, Asp28] Exendin-
4(1-39)-Lys6-NH2, des Met(O)14 Asp28 Pro36, Pro37, Pro38
Exendin-4(1-39)-NH2, H-(Lys)6-desPro36, Pro37, Pro38 [Met(O)14,
Asp28] Exendin-4(1-39)-NH2, H-Asn-(Glu)5-des Pro36, Pro37, Pro38 [Met(O)14,
Asp28] Exendin-4(1-39)-NH2, des Pro36, Pro37, Pro38 [Met(O)14, Asp28]
Exendin-4(1-39)-(Lys)6-NH2, H-(Lys)6-des Pro36, Pro37, Pro38 [Met(O)14,
Asp28] Exendin-4(1-39)-(Lys)6-NH2, H-Asn-(Glu)5 des Pro36, Pro37, Pro38 [Met(O)14,
Asp28] Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25] Exendin-4(1-39)-NH2, H-(Lys)6-des Pro36, Pro37, Pro38 [Met(O)14,
Asp28] Exendin-4(1-39)-NH2, H-Asn-(Glu)5-des Pro36, Pro37, Pro38 [Met(O)14,
Trp(O2)25, Asp28] Exendin-4(1-39)-NH2, des Pro36, Pro37, Pro38 [Met(O)14, Trp(O2)25,
Asp28] Exendin-4(1-39)-(Lys)6-NH2, H-(Lys)6-des Pro36, Pro37, Pro38 [Met(O)14,
Trp(O2)25, Asp28] Exendin-4(S1-39)-(Lys)6-NH2, H-Asn-(Glu)5-des Pro36, Pro37, Pro38 [Met(O)14,
Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Exemplary embodiments are described herein with reference to the drawings, in which:

In the following, a more detailed description of examples and embodiments of the drive mechanism is given in conjunction with the appended figures.

FIG. 1 shows a cross-section of an injection pen comprising an embodiment of the drive mechanism.

FIG. 2 shows a perspective view of the lead screw.

FIG. 3 shows a cross-section of the lead screw nut.

FIG. 4 shows an enlarged view of the distal end of the lead screw.

DETAILED DESCRIPTION

FIG. 1 shows a cut-away view of an injection pen comprising the drive mechanism. The drive mechanism is arranged in a body 1 having a distal end 2 and a proximal end 3. A lead screw 5 is arranged along an axis 4 of the device. A screw thread 6 of the lead screw 5 is coupled to a drive feature of a lead screw nut 7 engaging the screw thread 6, in order to guide a helical movement of the lead screw 5 with respect to the lead screw nut 7. In further embodiments, the screw thread and the drive feature can be reversed such that the lead screw is provided with discrete drive features and the lead screw nut is provided with a helical screw thread. The lead screw nut 7 is rotationally locked to the body 1.

The embodiment shown in FIG. 1 comprises a drive member 8, which can be operated by the user by means of a button 9, which is arranged at the proximal end 3 and juts out of the body 1. The drive member 8 is coupled or engaged with the lead screw 5. This is achieved, in this embodiment, by means of a screw thread 18 of the drive member 8 and a flexible guide feature 15 of the lead screw 5. The drive member 8 can especially be a drive sleeve of essentially cylindrical shape, the axis of the drive sleeve being arranged parallel to the axis 4 of the device. The lead screw 5 may be disposed to enter the drive member 8.

A removable and attachable part 11 of the body 1 may be provided as a cartridge holder. When this part 11 is removed from the rest of the body 1, a cartridge 12 can be inserted. When the part 11 is attached to the body 1, the lead screw 5 is brought into contact with a piston 13, which is provided to expel a drug from the cartridge 12. A bearing 14 may be arranged between the lead screw 5 and the piston 13 in order to prevent any damage that might be caused by a relative movement between the lead screw 5 and the piston 13. The lead screw 5 functions as a piston rod to advance the piston 13 in the distal direction.

During a delivery operation, the lead screw 5 is helically moved in the distal direction with respect to the body 1. The lead screw 5 is guided by the lead screw nut 7, which is engaged with the screw thread 6 of the lead screw 5. Stop features, described below, are provided in the screw thread 6 of the lead screw 5 to enable a set operation, by which a fixed dose that is to be dispensed can be preset. For this purpose, the drive member 8 is drawn in the proximal direction relatively to the body 1 and to the lead screw 5. The drive member 8 is coupled with the lead screw 5. In the embodiment shown in FIG. 1, the coupling is achieved with the screw thread 18 of the drive member 8 and the flexible guide feature 15 of the lead screw 5. During the set operation, the lead screw 5 must not be moved. Therefore, the engagement between the drive member 8 and the lead screw 5 is temporarily released during the set operation. This may be achieved by a deformation of the flexible guide feature 15 to override the screw thread 18 of the drive member 8. In spite of the engagement between the drive member 8 and the lead screw 5, the drive member 8 can therefore be moved without being rotated, while the lead screw 5 stays stationary with respect to the body. Overriding the engagement between the drive member 8 and the lead screw 5 is facilitated by flexible guide features 15, which can be bent towards the central axis 4. A rotation of the drive member 8 with respect to the body 1 may be prevented by guide features 10, which may be protruding elements of the body 1 engaging an axial groove in the outer surface of the drive member 8, for instance.

After the drive member 8 has been moved a distance corresponding to the pitch of the screw thread 18 of the drive member 8, the flexible guide feature 15 of the lead screw 5 reengages the screw thread 18 of the drive member 8, and the user can advance the lead screw 5 by pushing the drive member 8 back in the distal direction. This method of operation by disengaging and reengaging the lead screw 5 with the drive member 8 relies entirely on the lead screw 5 remaining substantially stationary during the setting operation. Should the lead screw rotate 5 or move axially during setting, then the drive member 8 would very likely not correctly reengage with the lead screw 5 and thus cause dose inaccuracy. Therefore, the lead screw nut 7 guiding the helical movement of the lead screw 5 with respect to the body 1 is rotationally locked to the body 1 at least during the dispense operation and, furthermore, the lead screw 5 is provided with stop features interfering with the rotation of the lead screw 5 in such a manner that the rotation is inhibited in the positions of the lead screw 5 which are obtained after the drug delivery and before the setting of a new dose. The rotation of the lead screw 5 is thus locked with respect to the lead screw nut 7, and the lead screw nut 7 is prevented from rotating relatively to the body 1. Therefore, when the drive member 8 is drawn in the proximal direction, the relative linear motion between the drive member 8 and the lead screw 5 causes the engagement of the drive member and the stationary lead screw 5 to be overridden and thus the engagement between the drive member 8 and the lead screw 5 to be released. The stop features are therefore preferably arranged at least on the distal sidewall of the screw thread 6 of the lead screw 5, while the screw thread 6 may be smooth, forming a helix, on its proximal sidewall. When the drive member 8 is pushed in the distal direction, a guide means of the lead screw nut 7 engaging the screw thread 6 of the lead screw 5 stays in contact with the smooth proximal sidewall of the screw thread 6, thus enabling a smooth helical movement of the lead screw 5 sliding through the opening of the lead screw nut 7. Therefore, the stop features do not interfere with the relative motion of the lead screw 5 with respect to the lead screw nut 7 during the dispense operation.

The stop features may especially be provided by recesses of a helical groove forming the screw thread 6 of the lead screw 5. The recesses can have contact faces arranged transverse to the axis 4 and interrupting the smooth helix of the relevant sidewall of the groove forming the screw thread 6. The contact faces may especially be flat portions, essentially perpendicular to the axis 4 or at least having zero helix angle, but may comprise a rake angle in the radial direction. A drive feature of the lead screw nut 7 may be formed in such a manner that it enters the recesses and stops on the contact face. When the drive feature of the lead screw nut 7 comes into contact with one of the flat portions, the generally perpendicular orientation of the flat portion with respect to the axis 4 causes the guidance of the helical movement of the lead screw 5 with respect to the body 1 to be stopped. It may be favorable if the drive feature of the lead screw nut 7 that engages with the screw thread 6 of the lead screw 5 and is stopped in the recesses is made up of one or more individual drive features and is not formed by a completely continuous helix. The stop features are arranged in such a fashion that, after a dose of the drug has been fully delivered and the device is ready for the next dose to be set, one of the stop features is in a position ready to stop the rotation of the lead screw 5 when the drive member 8 is pulled in the proximal direction. The axial load exerted on the lead screw 5 is then compensated by the drive feature of the lead screw nut 7 engaging the relevant stop feature, particularly contacting the essentially flat portion of the relevant recess. This acts to lock the rotation of the lead screw 5 rather than rotate it, because the lead screw nut 7 is rotationally locked to the body 1 at least during the operations of setting and dispensing a dose. Essentially, the flat surfaces on the screw thread 6 are designed to prevent a back-driving of the lead screw 5 during a set operation. The motion of the lead screw 5 may thereby be restricted to the distal direction.

FIG. 2 shows an enlarged perspective view of an embodiment of the lead screw 5. The lead screw 5 comprises a screw thread 6 and may comprise at least one further screw thread 16. If a further screw thread 16 is provided, the screw thread 6 and the further screw thread 16 have the same pitch and are intertwined. This means that the lead screw 5 has two co-axial helical features with separate entries at or near the distal end of the lead screw 5. The screw thread 18 of the drive member 8 may also have two separate co-axial helical features, which are intertwined. The shape of the flexible guide feature 15 at the proximal end of the lead screw 5 is adapted to the screw thread 18 of the drive member 8. The flexible guide feature 15 may especially comprise two co-axial helical male thread features provided to engage helical groves, which may form the screw thread 18 of the drive member 8. If there are two co-axial helical features of the screw thread 18, there may be two separate parts of the flexible guide feature 15, each of the parts engaging one of the helical features. The flexible guide feature 15 can be deformed and thus disengaged from the screw thread 18 of the drive member 8. This allows the coupling between the lead screw 5 and the drive member 8 to be temporarily overridden when the drive member 8 is pulled in the proximal direction.

FIG. 3 shows a cross-section of the lead screw nut 7. The drive feature 19 protruding from a surface 21 of the internal bore of the lead screw nut 7 may comprise a stop section 20, which is adapted to the form of the stop features of the lead screw 5. The drive feature 19 may comprise separate portions, which may each engage one of the screw threads 6, 16 of the lead screw 5. The drive feature 19 of the lead screw nut 7 may be tapered towards the screw thread 6 of the lead screw 5, as shown in FIG. 3. A tapered drive feature 19 may be especially advantageous in conjunction with a screw thread 6, 16 of the lead screw 5 that has a non-zero opening angle in the radial directions with respect to the central axis 4.

FIG. 4 shows an enlarged detailed view of the distal end of the lead screw 5. In this embodiment the lead screw 5 comprises a screw thread 6 and a further screw thread 16 with surfaces 23. The drive feature 19 of the lead screw nut 7 engages the screw threads 6, 16 of the lead screw 5 between the surfaces 23, which form a non-zero angle 22 in the radial directions 24. The set of screw threads 6, 16 at the distal end of the lead screw 5 have thus a buttressed form, i.e. the surfaces 23 providing the contact faces of the screw threads are angled rather than flat. This feature helps to ensure that the lead screw 5 remains central within the lead screw nut 7, and therefore central in the body 1, when a dose is dispensed. This reduces the risk of the lead screw 5 catching on the rim of the cartridge 12 and also facilitates the construction and assembly of the device.

The drive feature 19 of the lead screw nut 7 may especially comprise three separate portions, each having the shape of a thread feature. The portions may be approximately angularly equi-spaced on the inner surface of the internal bore of the lead screw nut 7. When the dispensing load of the lead screw 6 is reacted by the buttressed or tapered portions of the drive feature 19 of the lead screw nut 7, the geometry of the contacting thread surfaces creates a component of force from each of the three thread features towards the centre of the lead screw 5. Two or more portions of the drive feature 19 of the lead screw nut 7 may engage the same screw thread 6, 16 of the lead screw 5. Instead, each portion of the drive feature 19 may engage a different one of the screw threads 6, 16 of the lead screw 5.

The buttressed thread form and the intertwined separate co-axial helical structures are two features of the screw thread 6 of the lead screw 5 which help to improve the working of the mechanism, particularly to facilitate the relative movement of the lead screw 5 and the lead screw nut 7. These improvements can be obtained by implementing these features individually or in conjunction with one another

The invention claimed is:

1. A drive mechanism for a drug delivery device, comprising:
    a lead screw and a lead screw nut aligned with an axis defining an axial direction, and an opposite axial direction, and radial directions diverging from the axis,
    the lead screw comprising (i) a screw thread and (ii) at least one further screw thread, the screw thread and the at least one further screw thread having the same pitch and being intertwined, and
    a drive feature of the lead screw nut, the drive feature comprising three angularly equi-spaced drive portions;
    the drive feature engaging the screw thread and the further screw thread and allowing for a dispense operation of a fixed dose,
    the dispense operation comprising a helical movement of the lead screw with respect to the lead screw nut at least in the axial direction,
    the lead screw advancing a piston in a distal direction.

2. The drive mechanism according to claim 1, further comprising:
    a drive member rotationally locked with the lead screw nut,
    the lead screw being coupled with the drive member, the coupling generating a helical movement of the lead screw with respect to the drive member when the drive member is moved in the axial direction with respect to the lead screw, and the coupling being overridden to prevent a helical movement of the lead screw with respect to the drive member when the drive member is moved in the opposite axial direction with respect to the lead screw.

3. The drive mechanism according to claim 2, further comprising:
    a flexible guide feature of the lead screw, and
    a screw thread of the drive member,
    the flexible guide feature of the lead screw and the screw thread of the drive member providing the coupling of the lead screw with the drive member.

4. The drive mechanism according to claim 3, wherein the screw thread of the drive member has two separate co-axial helical features.

5. The drive mechanism according to claim 2, further comprising:
    stop features of the lead screw, the stop features inhibiting the helical movement of the lead screw when the drive member is moved in the opposite axial direction with respect to the lead screw.

6. The drive mechanism according to claim 1, wherein the drive feature of the lead screw nut comprises at least two separate parts protruding from an inner surface of the lead screw nut.

7. The drive mechanism according to claim 1, wherein the drive feature of the lead screw nut is tapered towards the screw thread of the lead screw.

8. The drive mechanism according to claim 1, wherein two or more portions of the drive feature of the lead screw nut engage a same screw thread of the lead screw.

9. A drug delivery device, comprising:
    a drive mechanism according to claim 1, and
    a body having a distal end and a proximal end, which are spaced apart in the direction of the axis.

* * * * *